(12) United States Patent
Sebastian et al.

(10) Patent No.: US 8,975,594 B2
(45) Date of Patent: Mar. 10, 2015

(54) MIXED-MATERIAL MULTISPECTRAL STARING ARRAY SENSOR

(71) Applicant: GE Aviation Systems LLC, Grand Rapids, MI (US)

(72) Inventors: Thomas Baby Sebastian, Chatham, NJ (US); Sarah Christine Maas Stotz, Ballston Lake, NY (US); Eric Daniel Buehler, Grand Rapids, MI (US); Benjamin Thomas Occhipinti, Grand Rapids, MI (US)

(73) Assignee: GE Aviation Systems LLC, Grand Rapids, MI (US)

( * ) Notice: Subject to any disclaimer, the term of this patent is extended or adjusted under 35 U.S.C. 154(b) by 211 days.

(21) Appl. No.: 13/673,045

(22) Filed: Nov. 9, 2012

(65) Prior Publication Data

US 2014/0132946 A1    May 15, 2014

(51) Int. Cl.
| | |
|---|---|
| *G01J 3/36* | (2006.01) |
| *G01N 21/25* | (2006.01) |
| *G01J 3/02* | (2006.01) |
| *G01J 3/08* | (2006.01) |
| *G01J 3/26* | (2006.01) |
| *G01J 3/28* | (2006.01) |
| *H04N 5/33* | (2006.01) |
| *G02B 27/10* | (2006.01) |
| *G02B 26/08* | (2006.01) |

(52) U.S. Cl.
CPC ............. *G01N 21/255* (2013.01); *G01J 3/0237* (2013.01); *G01J 3/021* (2013.01); *G01J 3/0256* (2013.01); *G01J 3/08* (2013.01); *G01J 3/26* (2013.01); *G01J 3/2823* (2013.01); *G01J 3/36* (2013.01); *H04N 5/332* (2013.01); *G01J 3/0208* (2013.01); *G01J 3/0229* (2013.01); *G01J 3/0294* (2013.01); *G02B 27/1013* (2013.01); *G02B 26/0816* (2013.01); *G01J 2003/2826* (2013.01)
USPC .......................................................... 250/394

(58) Field of Classification Search
CPC .... H04N 5/332; G01J 2003/2826; G01J 3/36; G01J 3/2823
See application file for complete search history.

(56) References Cited

U.S. PATENT DOCUMENTS

| | | | | |
|---|---|---|---|---|
| 4,678,332 | A | * | 7/1987 | Rock et al. ..................... 356/328 |
| 5,300,778 | A | | 4/1994 | Norkus et al. |

(Continued)

FOREIGN PATENT DOCUMENTS

| | | |
|---|---|---|
| EP | 0405051 A2 | 1/1991 |
| WO | 2012066741 A1 | 5/2012 |

OTHER PUBLICATIONS

EP Search Report and Written Opinion dated Mar. 5, 2014 issued in connection with corresponding EP Application No. 13191947.4-1562.

(Continued)

*Primary Examiner* — Constantine Hannaher
(74) *Attorney, Agent, or Firm* — General Electric Company; William S. Munnerlyn (57) ABSTRACT

A multispectral staring array comprises, amongst other things, at least two sensors where each sensor is adapted to detect an image in a different predetermined spectral sensitivity; a first lens to focus capture spectral bands; a spectral filter between the lens and the sensors to subdivide the incident spectral bands; and a second lens to direct and focus the subdivided incident spectral bands on each of the sensors.

10 Claims, 6 Drawing Sheets

(56) References Cited

U.S. PATENT DOCUMENTS

| | | | |
|---|---|---|---|
| 5,373,182 A | 12/1994 | Norton | |
| 5,587,784 A | 12/1996 | Pines et al. | |
| 5,729,011 A | 3/1998 | Sekiguchi | |
| 5,926,282 A | 7/1999 | Knobloch et al. | |
| 6,031,619 A * | 2/2000 | Wilkens et al. | 356/419 |
| 7,274,454 B2 | 9/2007 | Kowarz et al. | |
| 7,623,165 B2 | 11/2009 | Gruhlke et al. | |
| 7,949,019 B2 | 5/2011 | Bouma et al. | |
| 8,081,244 B2 | 12/2011 | Golub et al. | |
| 8,143,565 B2 | 3/2012 | Berkner et al. | |
| 2004/0218187 A1* | 11/2004 | Cole | 356/454 |
| 2006/0279647 A1* | 12/2006 | Wada et al. | 348/272 |
| 2007/0170359 A1 | 7/2007 | Syllaios et al. | |
| 2008/0137074 A1 | 6/2008 | Furman et al. | |
| 2009/0021598 A1 | 1/2009 | McLean et al. | |
| 2011/0194100 A1 | 8/2011 | Thiel et al. | |
| 2011/0254953 A1* | 10/2011 | Genio et al. | 348/135 |
| 2011/0279721 A1 | 11/2011 | McMahon | |
| 2011/0316982 A1 | 12/2011 | Steurer | |
| 2012/0038819 A1 | 2/2012 | McMackin et al. | |
| 2012/0127351 A1 | 5/2012 | Vlutters et al. | |
| 2013/0235256 A1 | 9/2013 | Kodama | |

OTHER PUBLICATIONS

European Search Report and Written Opinion issued in connection with corresponding EP Application No. 13191947.4-1562 on Jun. 5, 2014.

Haneishi et al., "Image acquisition technique for high dynamic range scenes using a multiband camera", Color Research & Application, Volume No. 31, Issue No. 4, pp. 294-302, Aug. 1, 2006.

* cited by examiner

MIXED-MATERIAL MULTISPECTRAL STARING ARRAY SENSOR

BACKGROUND OF THE INVENTION

Multispectral imaging systems collect and record electromagnetic energy in multiple distinct spectral bands, including light from the visible and near-infrared (VNIR), ultraviolet (UV) and infrared (IR) wavelengths of the spectrum. The resulting imagery is displayed by combining the spectral band information into one or many channels to form a grayscale or color representation of the image. Multispectral imaging devices are a class of spectrometers that record energy in many discrete spectral bands simultaneously on an image sensor at a multitude of spatial picture elements, called pixels. Standard broadband imagers record one value at each pixel for all the detected incident energy across a wide spectrum, and create an image in two spatial dimensions from a two-dimensional array of detectors. Multispectral imaging devices differ from standard broadband imagers by creating an image with an additional spectral dimension. Each multispectral pixel may have tens or hundreds of wavelength values recorded where each value is considered a subpixel. A staring array is one type of imaging device where two-dimensional array of detector elements at a focal plane captures energy in selected spectral bands so that an image can be directly constructed from the pixels and subpixels.

BRIEF DESCRIPTION OF THE INVENTION

One aspect of the invention relates to a multispectral staring array. The multispectral staring array comprises at least two sensors, each sensor adapted to detect an image in a different predetermined spectral sensitivity, and positioned on an image plane wherein the image planes are neither coplanar with nor parallel to each other; a first lens to focus incident spectral bands; a spectral filter between the first lens and the at least two sensors wherein the spectral filter is configured to subdivide the incident spectral bands; and a second lens configured to direct and focus the subdivided incident spectral bands on each of the at least two sensors.

DESCRIPTION OF EMBODIMENTS OF THE INVENTION

In the background and the following description, for the purposes of explanation, numerous specific details are set forth in order to provide a thorough understanding of the technology described herein. It will be evident to one skilled in the art, however, that the exemplary embodiments may be practiced without these specific details. In other instances, structures and device are shown in diagram form in order to facilitate description of the exemplary embodiments.

The exemplary embodiments are described with reference to the drawings. These drawings illustrate certain details of specific embodiments that implement the technology described herein. However, the drawings should not be construed as imposing any limitations that may be present in the drawings.

Technical effects of the multispectral staring array disclosed in the embodiments include greatly reducing the complexity of a sensing system that needs to gather both visible and infrared light. The consolidation of sensors reduces optical complexity and allows for the creation of a single multi-function semiconductor. Consequently, a multispectral imaging device implementing the staring array disclosed in the embodiments can be built into a smaller form factor with decreased weight and power requirements than its conventional counterpart. Additionally, the integration of different sensor types into a single semiconductor as disclosed in the embodiments of the current invention conserve the total light power available to the system that is typically lost due to complex light splitting techniques. By integrating sensors with different spectral sensitivities on a single semiconductor chip, the multispectral image device embodied in the present invention can form substantially real-time high dynamic range imagery. Finally, the embodiments of the multispectral staring array maintain sampling coherency.

Figure 1:
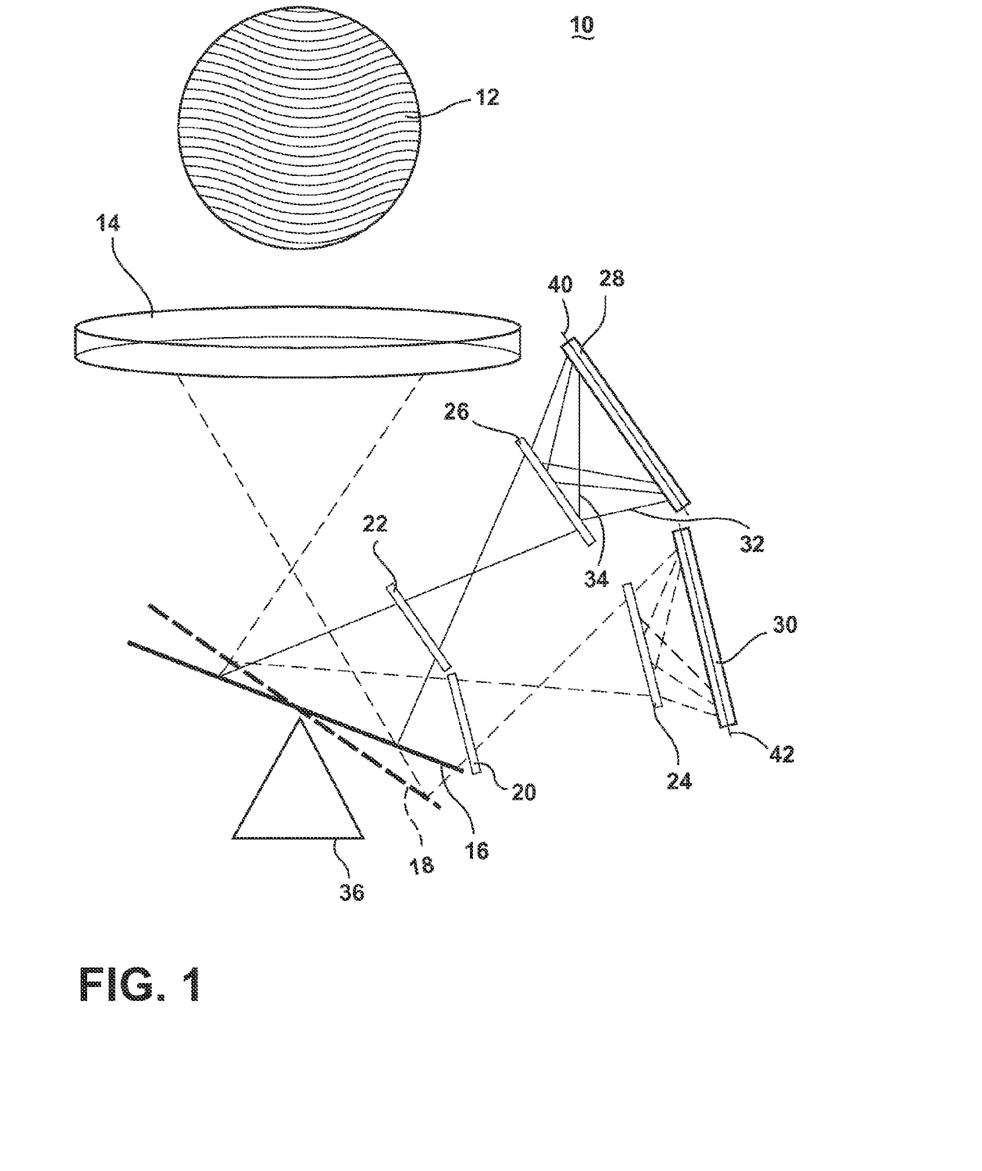
FIG. 1 is a schematic view of a multispectral staring array according to an embodiment of the present invention.

FIG. 1 illustrates a multispectral staring array 10 according to one embodiment of the present invention. The multispectral staring array 10 detects an image of an object 12 based upon the intensities of a set of bandwidths of the electromagnetic energy reflected or radiated from the object 12. The multispectral staring array 10 includes elements to isolate and detect spectral bands with varying spectral sensitivity. Spectral sensitivity is the relative efficiency of detection of light as a function of the light's wavelength. The bandwidth of the detected light is determined by the span of wavelengths where the spectral sensitivity is not zero. Elements of the multispectral staring array that may affect the spectral sensitivity of the detected incident light include spectral filters 20, 22, lenses such as microlens arrays 24, 26, and sensors 28, 30. The sensors are preferably mixed-material sensors capable of detecting light in wavelengths from multiple portions of the VNIR, UV and IR spectra. Alternatively, each sensor may be capable of detecting light in wavelengths from a single portion of the VNIR, UV and IR spectra. In this implementation, additional spectra may be detected by adding additional sensors. Additionally, the multispectral staring array 10 includes image forming optical elements that may include a lens 14 and a mirror 16. It is understood that the number and arrangement of the optical elements in the multispectral staring array may differ depending upon the implementation.

The array 10 includes an input aperture such as a lens 14. The lens 14 is configured to collect incident electromagnetic energy. As shown in FIG. 1, electromagnetic energy is transmitted through the lens 14 to a mirror 16. The electromagnetic energy is reflected by the mirror 16 and passes through a spectral filter 22. Because the spectral filter's wavelength response varies as a function of location, the spectral filter 22 is configured to subdivide the broadband electromagnetic energy into a set of spectral bands.

The subdivided spectral bands of electromagnetic energy then arrive at a microlens array 26. Each microlens of the microlens array 26 directs and focuses the subdivided spectral bands of electromagnetic energy onto the sensor 28 as shown by the set of rays such as 32 and 34 from the microlens array 26 to the sensor 28. The sensor 28 is positioned on an image plane 40 to the spectral filter 22. The sensor 28 is an array of detectors where each detector may be configured to detect electromagnetic energy of a spectral band with a predetermined spectral sensitivity.

The configuration of the spectral filter 22, microlens array 26 and the sensor 28 is such that each detector in the array will detect electromagnetic energy of a particular spectral band that corresponds to a segment of the imaged object 12. In this way, the sensor 28 includes detector elements arranged to form a multispectral pixel of the imaged object 12. The set of the detector elements on the sensor 28 that detects incident electromagnetic energy reflecting or radiating from a particular area of an imaged object 12 form a multispectral pixel.

As shown in FIG. 1, a driver 36 such as a gimbal mount may actuate the mirror 16 to a second position 18. Alternatively, a deformable mirror may be implemented to actuate from a first alignment to a second alignment to affect the redirection of the optical path from the first position of the mirror 16 to the second position of the mirror 18. The optical path of the electromagnetic energy may then proceed, by way of free space propagation or light pipe, from the mirror at 18 to a second spectral filter 20. Like the first spectral filter 22, the second spectral filter 20 is configured to subdivide the broadband electromagnetic energy into a set of spectral bands. The subdivided spectral bands of electromagnetic energy then arrive at a second microlens array 24 and are imaged onto a second sensor 30. The second sensor 30 is positioned on an image plane 42.

The redundant elements of the second spatial filter 20, the second microlens 24 array and the second sensor 30 allow for a highly configurable imager. The second spectral filter 20 may be configured to have a different wavelength response than the first spectral filter 22. Similarly, the second sensor 30 may consist of an array of detectors where each detector is configured to detect a set of spectral bands with a different spectral sensitivity than the analogous detector of the first sensor 28. In this way, the multispectral staring array 10 may achieve a higher spectral resolution, that is, detect a higher number of spectral bands per pixel than using a single optical path from the mirror 16 to the first sensor 28 by way of the first spectral filter 22 and the first microlens array 26.

Alternatively, the multispectral staring array 10 may achieve a higher dynamic range, that is, an expanded limit of detectable luminance, than using a single sensor by using two sensors 28 and 30 with different spectral sensitivities for the same spectral bandwidth. Additionally, according to an embodiment of the present invention, the multispectral staring array 10 may further augment high dynamic range (HDR) imaging by altering the timing of the mirror toggling. For example, the mirror at 16 would spend a relatively short time at a first position 16 to enable sensor 28 to capture variance of luminance of the scene in bright regions of the image and a relatively longer time at a second position 18 to enable sensor 30 to capture variance of luminance of the scene in the dark regions of the image.

Figure 2:
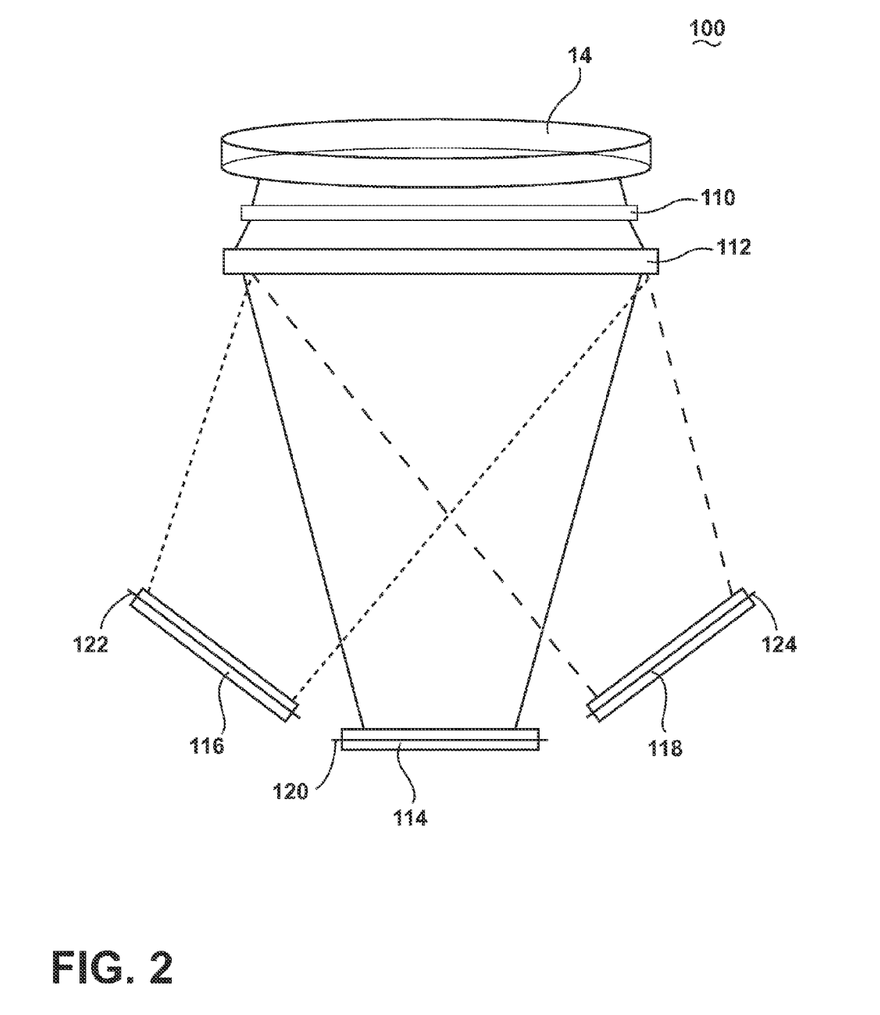
FIG. 2 is a schematic view of a multispectral staring array according to another embodiment of the present invention.

FIG. 2 illustrates a multispectral staring array 100 according to another embodiment of the present invention. The input aperture includes the lens 14 to focus incident light. The light passes through a spectral filter 110 that is configured to subdivide the incident spectral bands.

The subdivided spectral bands of electromagnetic energy then arrive at a microlens array 112. Each microlens of the microlens array 112 directs and focuses the subdivided spectral bands of electromagnetic energy onto one of the three sensors 114, 116 and 118. In this way, the microlens array 112 is acting in the same capacity as the actuating mirror 16, 18 in FIG. 1. A first subset of microlenses in the microlens array 112 may direct and focus the subdivided incident spectral bands to a first sensor 114 positioned on an image plane 120. Similarly, second and third subsets of microlenses of the microlens array 112 may direct and focus the subdivided incident spectral bands to second and third sensors 116, 118 respectively positioned on image planes 122 and 124. As in the embodiment of FIG. 1, each sensor may consist of an array of detectors configured to detect a different set of predetermined spectral sensitivities, thereby enhancing the spectral resolution or the dynamic range of the multispectral staring array 100.

Figure 3:
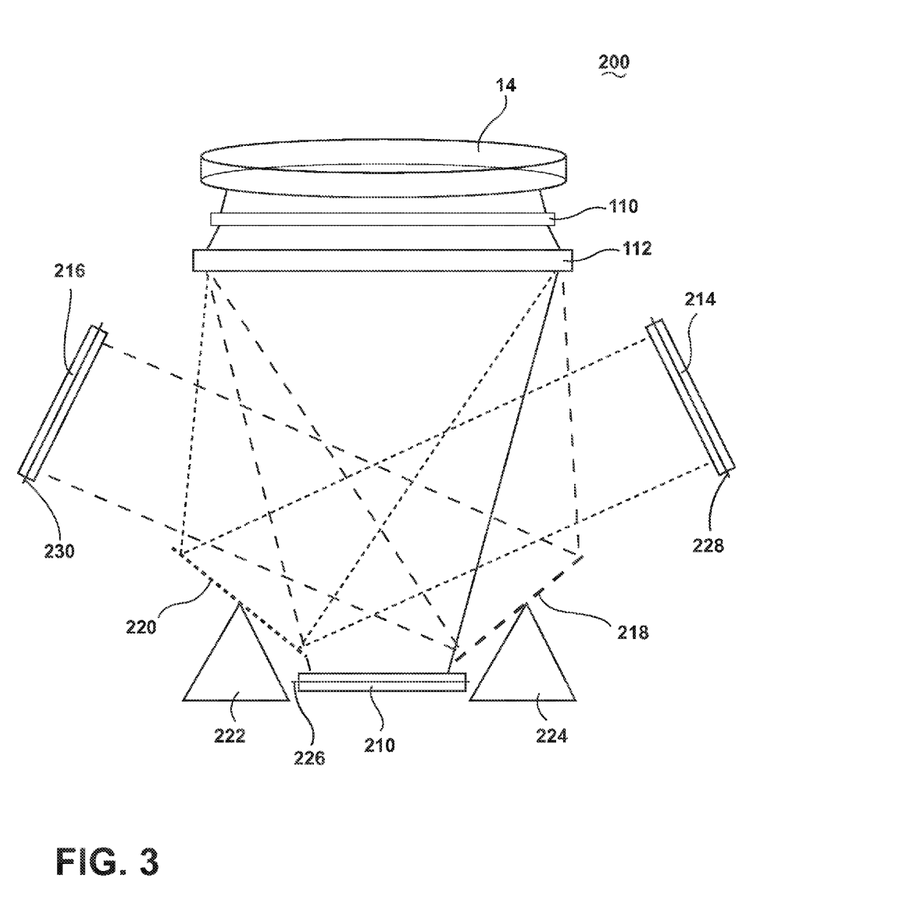
FIG. 3 is a schematic view of a multispectral staring array according to yet another embodiment of the present invention.

FIG. 3 illustrates a multispectral staring array according to yet another embodiment of the present invention. As in FIGS. 1 and 2, the input aperture includes the lens 14 to focus incident light. As in FIG. 2, the light passes through a spectral filter 110 that is configured to subdivide the incident spectral bands and the subdivided spectral bands of electromagnetic energy then arrive at a lens such as microlens array 112. Each microlens of the microlens array 112 directs and focuses the subdivided spectral bands of electromagnetic energy onto one of the three sensors 210, 214, 216 each positioned on an image plane 226, 228 and 230. In this embodiment of the present invention, the optical path to sensors 214 and 216 include a reflection off of mirrors 220 and 218 respectively.

As in the embodiment of FIG. 2, the sensors 210, 214 and 216 may be configured to affect different spectral sensitivities. The mirrors 218, 220 are held statically by mounts 222 and 224. As a result, without the requirement to actuate a mirror from position to position, the three sensors 210, 214 and 216 may detect the image simultaneously. However, the mirrors 218 and 220 may be actuated to configure the amount of time that light hits a sensor 214, 216 to augment HDR imaging as previously disclosed.

Figure 4:
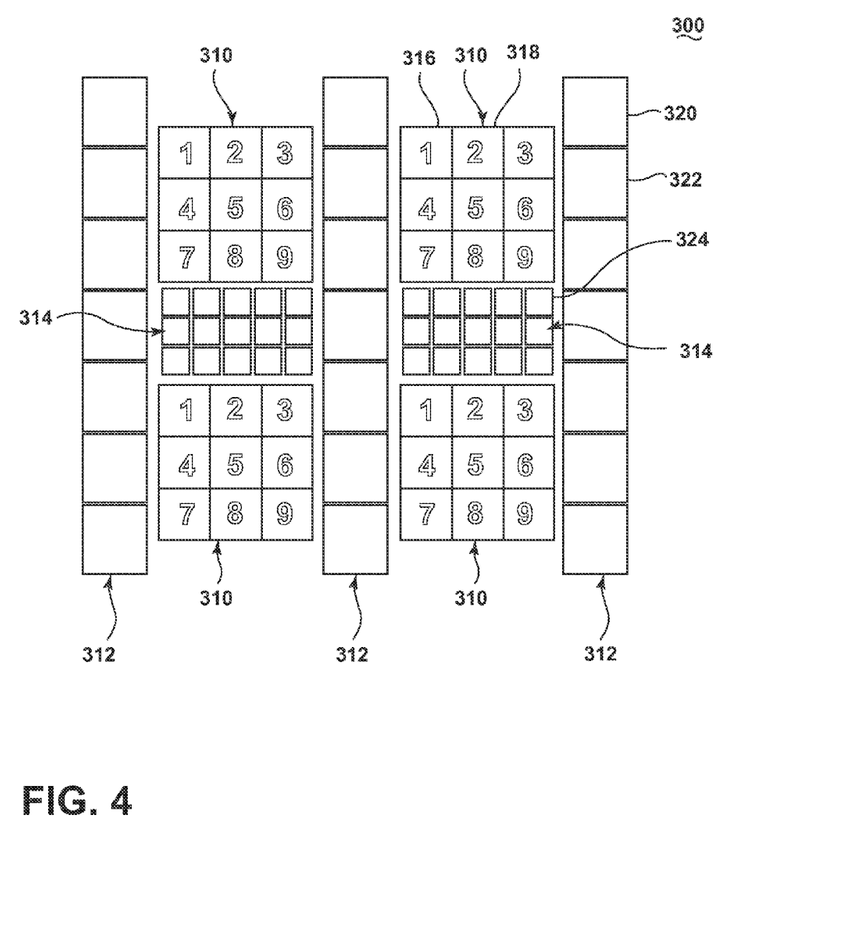
FIG. 4 is a schematic view of a mixed-material detector according to an embodiment of the present invention.

To enable the embodiments of the invention, the sensor as in 28 and 30 in the embodiment of FIGS. 1, 114, 116 and 118 in the embodiment of FIGS. 2 and 210, 214 and 216 in the embodiment of FIG. 3 may include detector elements with different spectral sensitivities or mirrors tuned with different actuation times. FIG. 4 illustrates a mixed-material sensor 300 according to an embodiment of the present invention capable of responding to a set of spectral bands ranging from the IR through VNIR and into the UV spectrum. The sensor 300 is a mixed-material staring array imaging semiconductor. The semiconductor has one or more instances of a VNIR detector array 310, IR detector array 312, and UV detector array 314. The different types of detectors are integrated into a single semiconductor and are coplanar. Each of the detector arrays 310, 312, and 314 is made of a number of detector elements that will comprise the subpixels of the image. Each element is responsive to a spectral band that may be a subset of the spectral band for the detector array. For example, the VNIR detector array 310 is shown in FIG. 4 to be made of nine subpixel elements such as 316 and 318. Each of the nine elements may be responsive to a different subband in the VNIR spectrum. Depending upon the implementation, each of the array elements of a particular detector array may be responsive to a spectral subband unique to the subpixels in the particular detector array. However, in some implementations, each of the subpixels in a detector array may be responsive to the same spectral band. In these implementations, a spectral filter such as 22 in the embodiment of FIG. 1 may filter the spectral band of electromagnetic energy incident on a particular subpixel. In one embodiment of the present invention, the filtered spectral bands, whether through configuration of the spectral filter or the mixed-material sensor or the combination of the two, are contiguous to render the multispectral staring array into a hyperspectral imaging device.

Figure 5:
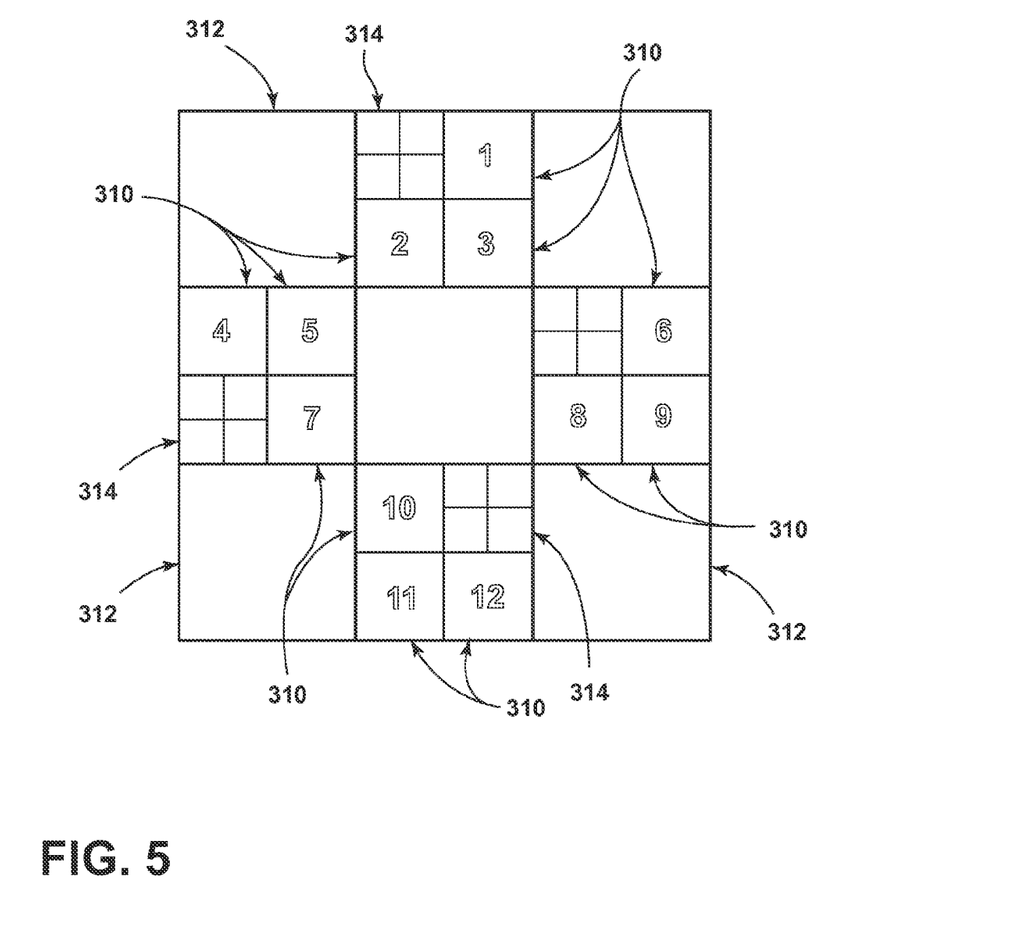
FIG. 5 is a schematic view of a mixed-material detector according to another embodiment of the present invention.

In another embodiment of the mixed-material sensor as shown in FIG. 5, the VNIR detector array 310, IR detector array 312, and UV detector array 314 elements are tessellated into a simple pattern that uniformly distributes the different light detector arrays 310, 312 and 314. The physically larger IR detector array 312 elements may be alternatively stacked with a comparable sized combination of UV detector array 314 elements and VNIR detector array 310 elements. As shown in FIG. 5, the VNIR detector array 310 is shown to be made of twelve subpixel elements. Each of the twelve elements may be responsive to a different subband in the VNIR spectrum. Other configurations of the detector arrays are possible depending upon the implementation. While the configuration shown in FIG. 5 may result in spatially uniform sampling of the scene for the different spectral bands, other configurations may be desired depending upon specific optical design parameters.

Figure 6:
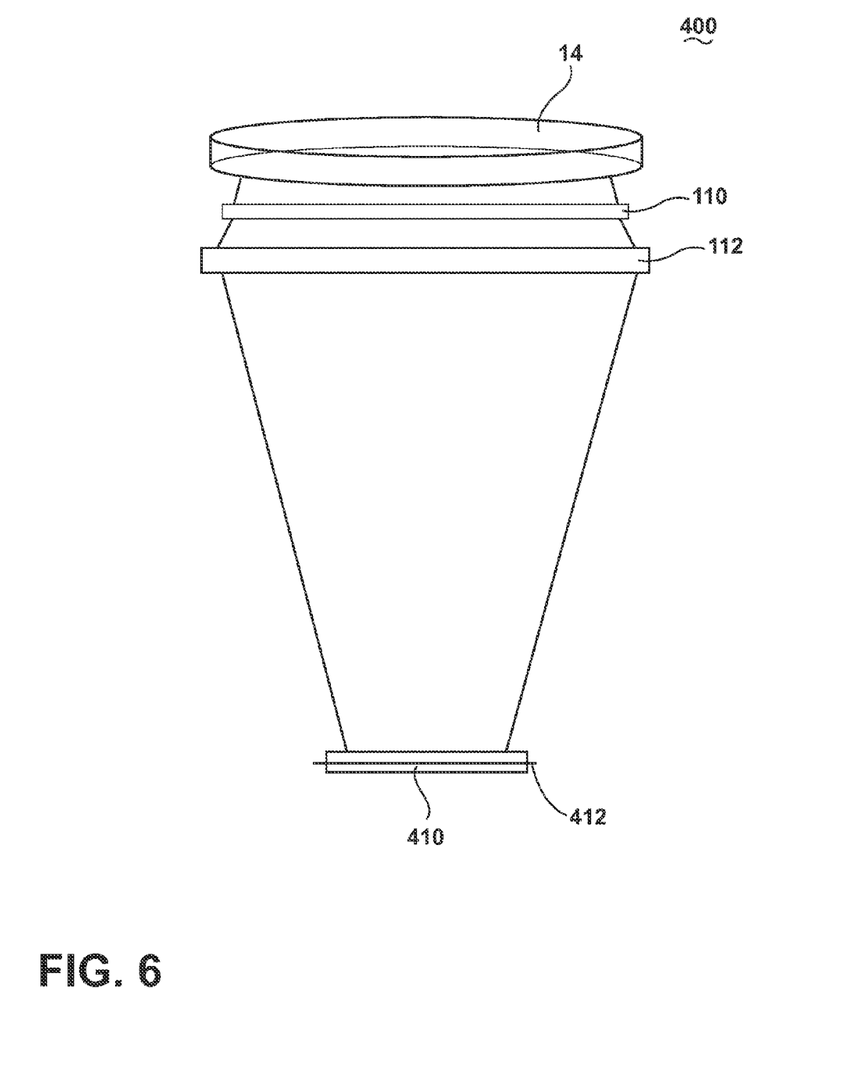
FIG. 6 is a schematic view of a multispectral staring array with a mixed-material detector from FIG. 4 of FIG. 5 according to an embodiment of the present invention.

Many semiconductor materials are known to be used in the manufacture of imaging detectors. In any embodiment of the present invention, these materials may be combined on a single chip. For example, the UV and VNIR wavelength detectors 310, 314 may be based upon variants of charge-coupled devices (CCD) or complementary metal-oxide-semiconductor detectors (CMOS). The IR detectors 312 may be a photodetector built from telluride, indium, or other alloys and incorporated with the VNIR and UV detectors 310, 314. When stacking detector types on the same semiconductor with a common substrate for the detector types such as silicon, the detectors are created on the same base wafer using multiple doping and etching steps to produce a layered mixed wavelength photodetector. For example, the UV detector 314 may be built upon the gate drains of the CCD-based VNIR detector 310. FIG. 6 illustrates a multispectral staring array with a mixed-material detector from the embodiment of FIG. 4 or FIG. 5 according to an embodiment of the present invention. While any of the embodiments of the multispectral staring array in FIGS. 1-3 may be implemented with a mixed material sensor 300 exemplified in FIG. 4 or FIG. 5, the multispectral staring array 400 with a mixed-material detector in FIG. 5 demonstrates a particularly simple embodiment of the present invention. The input aperture includes the lens 14 to collect incident light. The light passes through a spectral filter 110 that is configured to subdivide the incident spectral bands. The subdivided spectral bands of electromagnetic energy then arrive at a lens such as a microlens array 112. Each microlens of the microlens array 112 directs and focuses the subdivided spectral bands of electromagnetic energy onto the mixed-material sensor 410. The microlens array 112 is used to direct and focus light incident on the mixed-material sensor 410 to each of the detectors such as 310, 312 and 314 of the embodiment of FIG. 4 or FIG. 5, thereby ensuring deterministic coverage and physical assignment of pixels. The sensor 410 is positioned on an image plane 412. This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A multispectral staring array comprising:
at least two sensors, each sensor adapted to detect an image in a different predetermined spectral sensitivity, and positioned on an image plane wherein the image planes are neither coplanar with nor parallel to each other;
a first lens to capture incident spectral bands;
a spectral filter between the first lens and the at least two sensors wherein the spectral filter is configured to subdivide the incident spectral bands; and
a second lens configured to direct and focus the subdivided incident spectral bands on each of the at least two sensors.

2. The array of claim 1 where the at least two sensors are on a single chip.

3. The array of claim 1 where the seconds lens is a microlens array.

4. The array of claim 3 where the spectral filter is between the first lens and the microlens array.

5. The array of claim 3 further comprising a light pipe between the microlens array and each of the at least two sensors.

6. The array of claim 3 further comprising a fixed mirror to direct light from the microlens array to each of the at least two sensors.

7. The array of claim 1 further comprising an actuating mirror between the first lens and the spectral filter.

8. The array of claim 1 further comprising a deformable mirror between the first lens and the spectral filter.

9. The array of claim 1 wherein the predetermined spectral sensitivity is maximized in at least one of visible and near infrared (VNIR), ultraviolet (UV), and infrared (IR).

10. The array of claim 1 wherein the incident spectral bands are contiguous.

* * * * *

UNITED STATES PATENT AND TRADEMARK OFFICE
CERTIFICATE OF CORRECTION

PATENT NO. : 8,975,594 B2  
APPLICATION NO. : 13/673045  
DATED : March 10, 2015  
INVENTOR(S) : Sebastian et al.

Page 1 of 1

It is certified that error appears in the above-identified patent and that said Letters Patent is hereby corrected as shown below:

In the Specification

In Column 4, Line 37, delete "FIGS. 1," and insert -- FIG. 1, --, therefor.

In Column 4, Line 38, delete "FIGS. 2 and 210," and insert -- FIG. 2, 210, --, therefor.

In the Claims

In Column 6, Line 32, in Claim 3, delete "seconds" and insert -- second --, therefor.

Signed and Sealed this  
First Day of September, 2015

Michelle K. Lee  
*Director of the United States Patent and Trademark Office*